United States Patent [19]

Olson

[11] 4,411,795

[45] Oct. 25, 1983

[54] PARTICLE ADSORPTION

[75] Inventor: Wayne P. Olson, Valencia, Calif.

[73] Assignee: Baxter Travenol Laboratories, Inc., Deerfield, Ill.

[21] Appl. No.: 238,410

[22] Filed: Feb. 26, 1981

Related U.S. Application Data

[63] Continuation-in-part of Ser. No. 128,617, Mar. 10, 1980, abandoned.

[51] Int. Cl.³ .............................................. B01D 15/00
[52] U.S. Cl. .................................. 210/679; 210/692; 210/908
[58] Field of Search ............... 210/679, 691, 692, 908; 521/29

[56] References Cited

U.S. PATENT DOCUMENTS

| | | | |
|---|---|---|---|
| 3,706,661 | 12/1972 | Tangen et al. | 210/24 |
| 3,799,342 | 3/1974 | Greenspan | 210/73 |
| 3,865,731 | 2/1975 | Seitz | 210/359 |
| 3,917,527 | 11/1975 | Shaltiel | 210/31 C |
| 3,922,432 | 11/1975 | Renn | 428/327 |
| 3,959,128 | 5/1976 | Harris | 128/214 R |
| 3,960,720 | 6/1976 | Porath et al. | 260/112.5 R |
| 3,972,812 | 8/1976 | Gresl, Jr. | 210/77 |
| 4,004,587 | 1/1977 | Sheldon | 128/214 |
| 4,006,059 | 2/1977 | Butler et al. | 195/68 |
| 4,007,113 | 2/1977 | Ostreicher | 210/23 |
| 4,007,114 | 2/1977 | Ostreicher | 210/23 |
| 4,007,138 | 2/1977 | Kanig | 521/29 |
| 4,057,499 | 11/1977 | Buono | 210/136 |
| 4,059,512 | 11/1977 | Harris | 210/24 |
| 4,064,042 | 12/1977 | Kunin | 210/40 |
| 4,118,554 | 10/1978 | Fields | 526/15 |
| 4,148,869 | 4/1979 | Deaton | 424/1 |
| 4,168,300 | 9/1979 | Andersson et al. | 210/679 |
| 4,178,438 | 12/1979 | Haase et al. | 536/30 |
| 4,202,775 | 5/1980 | Tsutomu et al. | 210/287 |
| 4,248,685 | 2/1981 | Beede | 204/159 |
| 4,251,632 | 2/1981 | Chen et al. | 435/180 |
| 4,266,032 | 5/1981 | Miller et al. | 435/241 |
| 4,272,617 | 6/1981 | Kaetsu et al. | 435/182 |

FOREIGN PATENT DOCUMENTS

| | | |
|---|---|---|
| 1318570 | 5/1973 | United Kingdom . |
| 1542982 | 3/1979 | United Kingdom . |
| 2009623A | 6/1979 | United Kingdom . |

OTHER PUBLICATIONS

Selsted et al., "Infection and Immunity", 30(3):887–889, (Dec. 1980).
Berg et al., "Viruses in Water", pp. 52–53, 91–138 and 168–171, (1976).
Mix et al., "Dev. Ind. Microbiol.", 15:136–142, (1974).
Miles, "Hydrophobic Chromatography: A Bibliography", (1979).
Fletcher et al., "Colloid and Interface Science, Proceedings", 3:459–467, (1976).
Cuatrecasas et al., "Ann. Rev. Biochem.", 40:274–275, (1971).
Rohm and Haas Company, "Ambergard TM XE 352", (believed to have been publically available in 1978–1979).
Pertsovskaya et al., "Biologicheskie Nauki", 14(3):100–105, (1971), including translation.
Tanny et al., "J. Par. Drug Assoc.", 33:40–51, (Jan.–Feb. 1979).
Hjerten et al., "J. Chromatography", 101:281–288, (1974).
Magnusson et al., "Immunology", 36(3):439–447 (Mar. 19, 1979).
Halperin et al., "Biochemical and Biophysical Research Communications", 72(4):1497–1503, (1976).
VenKatsubramanian, "Immobilized Microbial Cells", pp. 28–57, (1978).
J. Parenteral Drug Assoc., V32(6): 258–267, 1978.

*Primary Examiner*—Ivars C. Cintins
*Attorney, Agent, or Firm*—Paul C. Flattery; Lawrence W. Flynn; Max D. Hensley

[57] ABSTRACT

Lipin particles are removed from aqueous suspension by adsorption on hydrophilic macromolecules substituted with pendant hydrophobic groups. Particularly beneficial results are achieved by use of pendant hydrophobes linked by strongly ionogenic groups to water insoluble carriers.

21 Claims, No Drawings

PARTICLE ADSORPTION

CROSS-REFERENCE TO RELATED APPLICATION

This application is a continuation-in-part of U.S. patent application Ser. No. 128,617, filed Mar. 10, 1980, now abandoned.

BACKGROUND OF THE INVENTION

This invention is concerned with the separation of lipin-containing particles from aqueous milieu. More specifically this invention relates to the removal of lipoprotein or glycolipid-containing vesicles from aqueous suspensions. This invention is particularly concerned with the general, nonspecific adsorption of microbes such bacteria, yeast, fungi and viruses from contaminated aqueous suspensions.

Lipins are a group of compounds comprising fats and lipoids which are soluble in ether. They include fats, fatty oils, essential oils, waxes, sterols, phospholipids, glycolipids, sulfolipids, aminolipids, chromolipids, fatty acids and lipoproteins.

A great variety of biological structures contain lipins. For example, particles such as animal viruses may contain lipids at up to about 50 percent by weight. Chylomicons, a major circulating lipid transport medium in higher animals, are essentially fat globules enveloped by a lipoprotein membrane. Animal cells, bacteria, yeast and fungi all contain varying proportions of lipins in their cell walls and protoplasm.

Chylomicrons, liposomes, cellular microorganisms and animal cells are examples of lipin vesicles, a major class of lipin-containing particles with which this invention is concerned. Lipin vesicles are generically defined as substantially water insoluble particles ranging about from 250 to 10,000 A in mean diameter which are characterized by a lipin-containing membranous envelope enclosing a liquid interior. The contained liquid may consist almost entirely of lipid, as in the case of chylomicrons, or be relatively free of the substance, as in the case of microorganisms. It is not necessary that the contained liquid have any lipid content whatsoever.

The presence of such lipin particles in aqueous suspensions has presented many problems for a great variety of arts. The foremost difficulty has been encountered with microbial contamination of aqueous liquids intended for administration to living organisms, particularly parenteral fluids infused into patients. While parenteral fluids are carefully manufactured so as to be sterile it is common practice for users to add medications or other additives to the solutions. This provides a potential avenue for contagion to enter the patient's blood stream. Thus it has been previous practice to modify the parenteral solution administration sets which are used to provide a controlled fluid flow from the solution container to the patient's vein by the inclusion of a filter capable of physically entrapping cellular microorganisms. Similar filters have been used with solution administration sets in continuous ambulatory peritoneal dialysis. Such filters, hereinafter referred to as sterile filters, are generally porous membranes having an average pore diameter of about from 0.2 to 0.45 microns, ordinarily about 0.2 microns. These filters are capable of retaining most cellular microorganisms since the smallest bacterium is believed to be about 0.3 microns in diameter.

The pharmaceutical industry has also employed membrane filters of this type to sterile filter products which cannot be chemically or thermally sterilized because of their lability. Examples of such products include insulin and human blood protein fractions such as factor VIII.

Sterile filters approach the absolute in retaining particles greater than the stated pore size. However they are readily clogged by relatively small numbers of particles, particularly those which have a pore size close to the average pore size of the filter. Consequently, it is conventional to pass the liquid to be sterilized through a depth filter before contacting it with the sterile filter. These filters have a high capacity to retain particles throughout rather than by sieving only at the liquid-filter interface.

Depth filters are fabricated from many materials including cellulose, polypropylene, diatomaceous earth and asbestos. Most of the depth filters trap particles by physical entrapment at points where two or more fibers or granules form a pore, alone or in combination with what usually are assumed to be London-van der Waal's attractive forces. Depth filters have the advantage of removing particles while retaining a high filter flux, i.e., a high flow rate of feedstock per unit of filtration area, even in the face of a particle load that would rapidly clog a sterile filter. However, depth filters are largely ineffective in removing particles in the 0.5 to 3 micron size range, at least when compared to sterile filters. Of course, viruses are too small to be retained even by sterile filters. A long felt need has existed for a unitary filter which is capable of removing particles having a wide range of sizes from suspension, including particularly bacteria and viruses, without suffering a significant reduction in flux when exposed to heavy particle loads. At the very least, considerable improvement could be secured by using a depth filter having such characteristics, thus freeing the sterile filter from its role as the virtually sole line of defense against passage of the smallest cellular organisms and thereby reducing the probability of clogging or flux reductions.

The sterile filters used in parenteral administration sets rarely have to deal with high levels of suspended particles, and thus clogging is not usually encountered. However, the flux of hydrocolloidal solutions such as blood protein fractions through sterile filters is very low. This low flux is attributed to the affinity of the hydrocolloids for the filter surfaces, resulting in increased hydrocolloid binding by the filter and the formation of hydrocolloid concentration gradients upstream from the filter surface. Similar problems are encountered in industrial sterile filtration of the same products. Consequently, membrane filters used in conventional parenteral administration sets for large-volume, non-colloidal parenterals such as dextrose or protein hydrolysates in water have proven inadequate for the filtration of viscous hydrocolloid solutions such as factor VIII or albumin.

Filters having small pores create another problem in parenteral solution administration. In the low pressure environment of an infusion any residual air in the administration set tubing will accumulate against the wetted filter rather than passing through. This phenomenon is termed air-blocking, and frequently it requires that the set be discarded. Efforts have been made to remedy this problem by inclusion of a non-wetting or hydrophobic filter in the set in addition to the normal hydrophilic member (U.S. Pat. No. 4,004,587). This of course necessitates the inclusion of two different types of filters in the set, an added expense.

Finally, all filters which rely solely upon the mechanical exclusion of particles depend upon the dimensional stability of the particles. If the particles can deform so as to pass through the micron sized pores of the filter then the filter will effectively fail. Mycoplasma, which are bacteria devoid of rigid cell walls, are highly deformable. Other families of microorganisms also exhibit varying degrees of deformation under pressure, as do mammalian cells and chylomicrons. The filtration of suspensions of such particles would be more reliable if mechanical exclusion could be supplemented.

In summary therefore it is apparent that the previous efforts of the art to remove particles from suspension primarily on the basis of mechanical exclusion has resulted in considerable difficulties.

Clinical chemistry is another art in which lipin particles have created problems. Blood samples taken for diagnostic assay of constituents are generally permitted to clot and the resulting serum removed by aspiration or decantation, frequently with the aid of devices such as disclosed in U.S. Pat. No. 3,865,731. While this process removes most cellular matter from the test sample it fails to reduce the level of other insoluble particles, most notably chylomicrons. Such particles interfere in subsequent optical assays of serum constituents.

An optical assay is defined as any analytical method in which the concentration or activity of an analyte is measured by a change in light as it is passed into the sample, and includes nephelometry and spectrophotometry in the main. Lipemic serum samples often contain chylomicrons in such concentrations that the serum appears milky, and even at lower chylomicron concentrations light scattering particles in the sample will interfere. While such samples may be diluted to reduce the interference this also necessarily dilutes the analyte, thereby reducing sensitivity, and in any case the comparative effect of the chylomicrons is still significant relative to analyte concentration. Reagents such as detergents may be added to destroy the lipid suspension but may interfere in various assays (United Kingdom Pat. No. 1,542,982). Ultracentrifugation will remove the particles but requires costly equipment and is tedious to perform. A need therefore exists for a method and device to remove lipin particles from biological fluids to be assayed by optical methods.

A need also exists in many arts to nonspecifically remove animal viruses from aqueous compositions. While the virions in many aqueous substances can be inactivated by pasteurization or chemical sterilization, many labile products, particularly pharmaceuticals and some blood protein fractions, are sensitive to such harsh treatments. These techniques are also not suitable for high volume treatments such as drinking water purification because of the high cost. Mechanical entrapment of virions by filtration ordinarily is not practical because at the required pore sizes the filter flux is extremely low.

Various investigators have looked into the use of immunoadsorbents to separate hepatitis virus. However, this technique is of little use because supplies of antihepatitis are limited, there is a risk of leaching antibody into the adsorbent effluent and, primarily, the antibody is necessarily capable of binding only the hepatitis virion and is not effective in removing other harmful viruses.

Immunoadsorbents have also been used in various affinity chromatography techniques for cell separation. See Cuatrecasas et al., "Ann. Rev. Biochem." 40:275 (1971). In these techniques inert matrices are substituted with ligands. Animal cells expected to contain membrane receptor proteins for the ligands are contacted with the immobilized haptens. Those cells having receptors specific for the ligand are bound while the remainder are washed free of the substrate, thus enabling one to obtain specific cell lines. Such methods are, however, of no use where the object is to remove a diverse cell population from suspension because the receptor sites are unknown and, in any case, would be so numerous that preparing immobilized ligands for all of them would be impractical.

This handicap would appear to be shared by the process of U.K. patent specification No. 1,531,558 to Kabi. This patent discloses adsorbing hepatitis virus from plasma and some solutions of blood protein fractions with a water permeable matrix having a coupled hydrophobic ligand of more than 7 carbon atoms or a condensed ring system. The adsorbent is disclosed to have a high and specific affinity for hepatitis virus. A need therefore remains for an adsorbent for animal viruses which is not specific for any one virus.

Tanny et al., "J. Parenteral Drug Association" 33(1):40–51 (1979) speculate that 0.45 and 0.20 micron cellulose triacetate membranes retain *Pseudomonas diminuta* by a combined adsorptive and sieve effect. Similarly, Tanny et al. advance the same hypothesis to account for losses in the titer of influenza vaccine passed through mixed cellulose esters, cellulose triacetate and acrylonitrile-vinyl chloride copolymer ["J. Parenteral Drug Association" 32(6):258–267 (1978)].

Pertsovskaya et al. "Biol. Nauki" 14(3):1005 (1971) disclose that glass, methylene and amine-substituted glass, and films of polyamide, polysacrylate, cellulose triacetate, and polyethylene all adsorb different groups of bacteria to varying degrees. In some cases, e.g., with bacilli, no adsorption at all was observed. Gerson et al. in *Immobilized Microbial Cells*, K.Ven Katsubramanian, Editor, pp 39–43 (1978) also report adsorbing various bacteria to surfaces.

Ambergard TM filters, which are ion exchange resins having the structure $R-N^+(CH_3)_3X$ wherein R is a styrenedivinylbenzene copolymer and X is $OH-$, $Cl-$ or $SO_4=$, have been used to upgrade the bacteriological quality of demineralized water for ultimate use in pharmaceuticals (Rhom and Haas literature dated June, 1978). In this connection, see U.K. patent application No. 2,009,623A.

U.S. Pat. Nos. 4,007,113 and 4,007,114 to Ostreicher employ a matrix of self bonding and electronegative fibers having surfaces coated with malamine-formaldehyde cationic colloid for filtering contaminated liquids.

Hjertén et al., "J. of Chromatography" 101:281–288 (1974) discloses that satellite tobacco necrosis virus and baker's yeast cells are retained in columns of non-ionogenic hydrophobic agarose in the presence of elevated salt concentrations.

Similarly, Magnusson et al. in "Immunology" 36:439–447 (Mar. 19, 1979) disclose that adsorption of *S. typhimurium* occurs when placed on a column in the presence of 1M $(NH_4)_2SO_4$, but that the bacteria elute as the salt concentration is reduced.

Halperin et al., "Biochemical and Biophysical Research Communications" 72(4):1497–1503 (1976) disclose desorbing erythrocytes retained on alkyl agarose columns by repeated pipetation in the presence of bovine serum albumin.

Accordingly it is an object of this invention to adsorb a wide spectrum of cells including animal cells, unicellular organisms, bacteria, yeast, fungi and viruses, from aqueous suspensions, using a single adsorbent composition.

It is another object to provide improved hydrophobic adsorbent compositions.

It is a further object of this invention to remove lipin particles from lipemic body fluids such as serum or plasma and provide an improved device therefor.

It is another object to pasteurize alcoholic beverages without the cost and detriment to flavor inherent in prior methods.

It is an additional object of this invention to sterile filter parenteral solutions, particularly solutions containing protein or low concentrations of salt, at increased flux and with greater assurance of sterility than heretofore possible, and to provide an improved device therefor.

It is another object to provide an improved surface for the cultivation of mammalian cells in tissue culture or for binding enzyme-containing lipin particles used in enzyme reactors.

These and other objects of this invention will be apparent from consideration of this specification as a whole.

SUMMARY OF THE INVENTION

It has now been found that hydrophilic moieties having pendant hydrophobic groups and strong ionogenic groups avidly adhere to a great variety of lipin particles, including animal virions, animal cells, bacteria, yeast, fungi and chylomicrons. Accordingly, certain of the objects of this invention are achieved by contacting an aqueous suspension of lipin particles with novel compositions having the formula $$[(Y)_e B]_d Z$$

wherein Y is a hydrophobic ligand, B is a strong ionogenic group, Z is a water insoluble carrier, e is an integer and d is greater than 2, and then separating the composition from the fluid.

Further, it has been found that adsorbent compositions having the formula $[(Y)_e B]_d Z$, wherein Y, Z, e and d are as described above and B is a linking group or bond, are capable of nonspecifically adsorbing aerosols of lipin particles or such particles from aqueous liquids containing proteins, ethanol or low ionic strength.

In addition, such adsorbent compositions have been found useful in mammalian tissue culture and as a binding medium for the adsorption of lipin vesicles having active enzymes for use in enzyme reactors.

DESCRIPTION OF THE PREFERRED EMBODIMENTS

The hydrophobic ligand Y is characterized broadly by its low solubility in water and its affinity for lipid solvents, primarily ether. Suitable hydrophobes are generally those in which, when the group BZ is replaced by methyl, the water solubility of the resulting compound at 20° C. will be less than about 0.075 parts by weight of the compound per 100 parts by weight of water and its solubility in ether at the same temperature will be infinite. Preferably this hypothetical compound will be insoluble in water in 20° C. Its molecular weight will range about from 70 to 600, ordinarily about from 100 to 400. On a molecular level the pendant hydrophobe should roughly appear as a cylinder having average dimensions of about from 7 to 40 A in length and about from 3 to 15 A; preferably about from 3 to 10 A, in diameter. The effect of the hydrophobe is generally less satisfactory as the diameter increases above about from 10 to 15 A, but the length is less material.

The hydrophobe-substituted adsorbents herein generally contain pendant hydrophobic ligands having the formula $$R - \left[ \left( \begin{array}{c} R \\ | \\ C \\ | \\ R \end{array} \right)_n - J - \left( \begin{array}{c} R \\ | \\ C \\ | \\ R \end{array} \right)_y \right]_b - A -$$

and wherein

R is hydrogen, nitro, alkyl, alkyl ether, halogen, monocyclic aromatic hydrocarbon or a carbocycle system;

A is a bond, monocyclic aromatic hydrocarbon or carbocycle system;

b is an integer;

J is oxygen, sulfur or a bond; and n and y are zero or an integer;

with the proviso that where A is a bond and R is hydrogen, nitro or halogen then the sum of n and y is an integer greater than 5.

Suitable carbocycle systems for the hydrophobe adsorbents are multiple hydrocarbon ring systems which may be fused or bridged, contain about from 4 to 30 carbon atoms and be saturated or unsaturated. Preferably the systems will contain about from 6 to 20 carbon atoms and be either aromatic or fully saturated. Examples of suitable bridged systems are bicyclo[2.2.1]heptane, bicyclo[3.2.1]octane, bicyclo[1.1.0]butane and bicyclo[2.2.1]hept-2-ene. Suitable spiro systems are spiro[2.3]pentane and spiro[3.4]oct-1 ene. The fused systems may be ortho or peri, preferably ortho such as naphthalene, indene, fluorene, arthracene and phenanthrene. Ortho fused systems having more than 3 rings, e.g. steroids such as cholesterol, may also be employed. Ring assemblies such as tercyclohexane and biphenyl are acceptable.

The monocyclic aromatic hydrocarbons useful in or as the pendant hydrophobic ligand will contain generally about from 6 to 12 carbon atoms, preferably 6-8 and are most desirably phenyl.

All R groups are preferably hydrogen, although substitution with nitro, alkyl, alkyl ether, halogen, monocyclic aromatic hydrocarbon or carbocycle systems is within the scope of this invention. Ordinarily, about from 1 to 3 R groups will be other than hydrogen, alkyl or alkyl ether. Suitable halogens are fluorine, chlorine or bromine, preferably fluorine. The monocyclic aromatic hydrocarbons or the carbocycle systems are usually singly substituted at the pendant hydrophobe terminus, with a monocyclic aromatic hydrocarbon preferred over a carbocyclic system. The branched chain systems which result from the use of alkyl R groups are generally satisfactory where R is a short chain alkyl or alkyl ether, on the order of $C_1$ to $C_6$.

Group J is preferably a bond. If J is other than a bond then the oxygen ether is preferred.

Generally n+y will range from 1 to about 20 in total, but each will tend to vary inversely with one another if X is oxygen or sulfur. The sum of n and y is usually about from 4 to 25, preferably 7 to 23 where A is a bond and R is H. The value for n+y preferably will be about from 1 to 10 it at least one R is an aromatic hydrocarbon or carbocycle system, and particularly when A is a bond and not a ring. Where J is oxygen or sulfur, n is usually greater than 2, particularly when no terminal R is an aromatic hydrocarbon or carbocycle system. Where A is a bond and R is hydrogen, nitro or halogen then the sum of n and y is greater than 5.

The number of Y groups, designed e, will depend upon the nature of the linking group chosen. Generally, e will range from 1 to about 3, with one being preferred.

The degree of major branching of the hydrophobic ligand is designed by b. In the preferred instance both b and e are 1 when A is a bond. When A is an aromatic hydrocarbon or carbocycle system the designation b indicates the degree of substitution of the aromatic hydrocarbon or carbocycle system. This degree of substitution is preferably low, with b ranging about from 1 to 4. This is particularly the case where an R group is an aromatic hydrocarbon or carbocycle system, or where n+y is greater than 5.

The preferred hydrophobes are long chain, normal, secondary or tertiary alkyl such as n-hexyl, n-octyl, n-dodecyl, n-tetradecyl, or n-octadecyl.

The degree of substitution of the hydrophilic macromolecule with pendant hydrophobic groups is represented by d, a minimum of 2 with a maximum dependent upon the characteristics desired in the adsorbent. The degree of substitution must be correlated with the size of the macromolecule Z, its hydrophilicity, i.e., the nature of the non-hydrophobic substituents of Z, the hydrophilicity of the linking groups B and the dimensions of the hydrophobe ligand. The adsorbent as a whole should be water wettable but not water soluble. Accordingly, d should not be so high as to render the material water repellant. Generally, the ratio of d to the number of hydrophilic groups that exist on the hydrophilic macromolecule at the pH, temperature and ionic conditions of adsorbent use, i.e., the number of exposed polar groups, will range about from 2:1 to 1:50. More specifically, when Z is an organic, hydrophilic polymer then d will range about from 0.5 to 0.1 times the number of monomer units constituting the polymer.

The BZ moiety functions as a hydrophile. The linking groups B, the water insoluble carrier Z, or both B and Z contain hydrophilic groups which impart several desirable properties to the adsorbent. First, permeation of aqueous suspensions into adsorbent matrices is facilitated by the overall water wettability of the matrices. Second, the adsorbent affinity for lipin particles is enhanced by the net hydrophilic character of the adsorbent when compared to entirely hydrophobic surfaces or those in which the hydrophobe is not pendant, i.e., branched from a hydrophilic matrix. Third, the presence of hydrophilic groups lessens the nonspecific binding of low molecular weight lipophilic compounds such as drugs and dyes. Fourth, the combined effect of ionic and hydrophobic binding enhances adsorption of lipin particles.

Z is a water insoluble carrier. It need not be hydrophilic so long as the linking groups render it water wettable or swellable after substitution with the pendant hydrophobic ligands. Also, the carrier conceivably may be so strongly hydrophilic and of such a molecular weight that it is water soluble before substitution. This, however, is not preferred since separation of the adsorbent from suspension after it has bound lipin particles is not as efficient as with highly water insoluble hydrophilic carriers. It is preferred that the carrier be an organic polymer containing a high density of hydrophilic groups.

The average molecular weight of the carrier which is desirable will vary widely as it depends upon a number of factors, including the carrier's hydrophilicity as reflected by the water adsorptive capacity of the hydrophobe-unsubstituted carrier, the extent of crosslinking within the carrier and the degree of hydrophobe substitution which is contemplated. For example, a suitable molecular weight for starch would be greater than that for crosslinked dextrans, which in turn would be greater than that needed for satisfactory performance with cellulose or nylon. Further, the average molecular weight needed for the carriers can be reduced as the degree of substitution by the pendant hydrophobes rises. Generally, the carrier will have a molecular weight of greater than about 1000, ordinarily about from 2000 to 2,000,000.

A principal function of the carrier is to provide physical integrity for the adsorbent, e.g., as a formed article, fibrous mass, woven textile or a membrane. This is an important function where the adsorbent is to be used in a filtration mode. Thus, carriers which have been crosslinked, for example by bisepoxide, glutaric dialdehyde, divinylsulfone, dibromopropanol or epichlorohydrin, are useful because of their more rigid structure.

The carriers should also be nonbiodegradable. Thus such materials as glass, silica, diatomaceous earth, agarose, polyvinyl alcohol, polyvinyl pyrrolidone, crosslinked dextrans, polyacrylamide, polystyrene, styrene-divinylbenzene copolymers and nylon are preferred. Less preferred in applications involving long-term use, because of susceptibility to attack by microbial enzymes, are starches, proteins and cellulose.

When adsorbing lipins from blood or blood fractions it is preferred to employ as carriers nylon, polyvinyl alcohol, lower alkyl esters of cellulose, polyvinyl pyrrolidone, polyacrylamide, polyanhydroglucose or polyacrolein. Nylon is most preferred for this purpose. On the other hand, for water purification cellulose, polyolefins and inorganic carriers such as glass or diatomaceous earth are preferred because of their comparatively low cost.

It should be noted that the carrier need not contain or be substituted with any hydrophilic groups at all if the linking groups bonding the pendant hydrophobe to the carrier are sufficiently numerous and hydrophilic to impart water wettability to the adsorbent. However, such an embodiment is not preferred.

The hydrophobe is always pendant, which means that it is branched from the carrier as a side chain. This is critical. The linking group found intermediate the carrier and hydrophobe is, however, optional so long as the carrier in such cases is hydrophilic. The linking group may be dispensed with, i.e., be a bond, when the hydrophobe is bound directly to the carrier, for example by copolymerization of a hydrophobe-substituted vinyl compound with a hydrophilic comonomer, or by radiation grafting. However, most of the convenient techniques for linking the hydrophobe to a carrier will deposit a hydrophilic residue between the hydrophobe and the carrier. Such linking groups include one or more of the groups oxo or thio ether, amido, ester, carboxyl, sulfonate, sulfone, imido, hydroxyl, thiourea, azo, silane, and amino (primary, tertiary or quaternary). Generally the hydrophilic linking groups will range about from 5 to 50 Å in length and have a molecular weight of about from 25 to 1000. Preferably, the group is about 10 Å long and has a molecular weight of about 200.

Either the carrier or the linking group must be hydrophilic, but the nature of the groups which provide the hydrophilic nature may vary considerably. They are conveniently placed into three functional categories: substantially nonionogenic, weakly ionogenic and strongly ionogenic. The category used will largely depend upon the desired function for the adsorbent, i.e. the solvent and lipin particles expected to be encountered.

Substantially nonionogenic substituents are defined for the purposes herein as those which have a pK of greater than about 12. Ordinarily, substituent groups such as hydroxyl, amido, ester, ether or silane will fall in this category. Carriers and linking groups which contain or are composed of these groups are preferably used to adsorb lipin particles from protein-containing fractions, from solutions intended for therapeutic administration, or from alcoholic beverages. They are also preferred when the physical integrity of lipin vesicles is to be maximized, i.e., in enzyme reactors and tissue culture. For such uses the preferred embodiments are polyamide or polyhydroxylated carriers, e.g., cellulose, nylon or polyvinyl alcohol, bound to the hydrophobe through an ether linking group.

Where maximum adsorption of lipin particles is desired, and where particle rupture or disintegration and changes in the ionic composition of the product are not so important then the carrier or linking group may contain or be composed of weak or strong ionogenic substituents. Weak substituents have a pK of about from 2 to 12. These are usually carboxyl, phosphoryl, or primary, secondary or tertiary amino groups.

Strong substituents have a pK of less than about 2. Examples are sulfonate or quaternary amino substituents. These substituents are particularly useful in water treatments because of a lipid structure biocidal effect that is similar to that of detergents in solution. It is preferred to use the hydroxide form of the quaternary amine as it will not contribute metal ions to be product. The acidic hydrophobic resins should be charged with pharmaceutically acceptable ions such as sodium or potassium.

The location of the ionogenic groups is not critical. However, they are optimally substituted immediately adjacent the pendant hydrophobic group, i.e., within about 10 Å. This is conveniently accomplished by providing linking groups which are themselves ionogenic, polyfunctional substituents. As examples, sulfonyl, tertiary or quaternary amino or phosphoryl groups may be linked through one functionality to the carrier and then substituted at least once with a hydrophobic group. In such cases the hydrophobic group is preferably normal alkane of 6, 8, 10 or more carbon atoms, up to about 20 carbon atoms, so as to minimize steric hinderance or simultaneous hydrophobic and ionic bonding of the lipin particle. Such linking groups are preferably employed with nonionogenic or weakly ionogenic hydrophilic carriers, or with hydrophobic carriers.

Disulfide or thioester linking groups are particularly useful because these groups may be cleaved, respectively, by reduction with dithiothreitol or by hydrolysis at pH 11.5 for 15 minutes. Thus any adsorbed particles can be recovered for further use or for destruction and the adsorbent then regenerated by reforming the labile linkage with fresh hydrophobe.

In a further embodiment, hydrophilic, pendant hydrophobe-substituted polymers may be adsorbed or covalently linked to other polymers. This enables the artisan to more carefully control the macroscopic character of any formed articles made from the adsorbents of this invention, in particular to improve their hydraulic shear resistance. It also multiples sites for binding the hydrophobes. For example, dextran-substituted glass may be prepared and covalently linked to hydrophobic moeities in accordance with known techniques. In such cases the composite macromolecule functions as the carrier of this invention.

It is within the scope of this invention to employ a plurality of different hydrophobes, linking groups and carriers and ionogenic groups within the same matrix. Where amphoteric adsorbents are employed, i.e., adsorbents substituted by both positively charged and negatively charged groups, all of which ordinarily have terminal hydrophobes, it is preferred that the populations be segregated into mosaics in the matrix rather than being substituted adjacent to one another on the same carrier. This is easily done by preparing differently charged matrices separately in finely divided form, followed by mixing.

Examples of suitable adsorbents which are contemplated are set forth in Table 1 below.

TABLE 1

Representative Adsorbents
d > 2

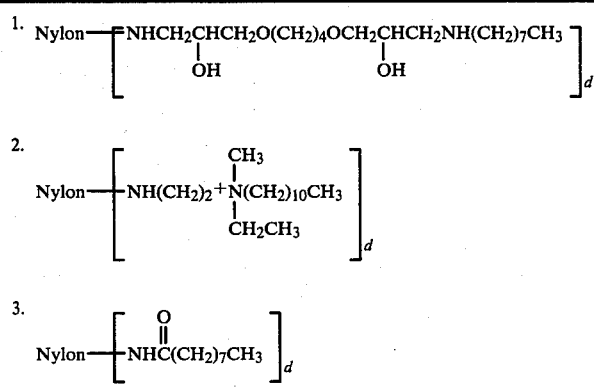

TABLE 1-continued
Representative Adsorbents
d > 2

4. Cellulose—[OCH$_2$CHCH$_2$O(CH$_2$)$_3$OCH$_2$CHCH$_2$O(CH$_2$)$_7$CH$_3$]$_d$
　　　　　　　　　|　　　　　　　　　　　|
　　　　　　　　OH　　　　　　　　　　OH 5. Agarose—[OCH(CH$_2$)$_{10}$CHClCH$_3$]$_d$
　　　　　　　|
　　　　　　COOH 6. Agarose—[OCH(CH$_2$)$_{10}$CH$_3$]$_d$
　　　　　　|
　　　　　COOH 7. Agarose—[O(CH$_2$)$_3$NHC(=O)(CH$_2$)$_2$CNH(=O)(CH$_2$)$_7$CH$_3$]$_d$ 8. Cellulose—[O(CH$_2$)$_3$NHC(=O)(CH$_2$)$_{12}$CH$_3$]$_d$ 9. Cellulose—[O(CH$_2$)$_3$C(=O)NH(CH$_2$)$_5$—⌬—(CH$_2$)$_2$CH$_3$]$_d$ 10. Cellulose—[OC(=O)—⌬—N=N(CH$_2$)$_{10}$SCH$_3$]$_d$ 11. Polyvinyl Alcohol—[O(CH$_2$)$_2$CHCH$_2$CH(C(=O)NH(CH$_2$)$_{10}$CH$_3$)(C(=O)—NH(CH$_2$)$_{10}$CH$_3$)]$_d$ 12. Cellulose—[OCH$_2$C(=O)NH(CH$_2$)$_3$NH(CH$_2$)$_3$NHC(=O)(CH$_2$)$_2$CNH(=O)(CH$_2$)$_{10}$CH$_3$]$_d$ 13. Cellulose—[O(CH$_2$)$_3$NHC(=O)(CH$_2$)$_2$CS(=O)(CH$_2$)$_7$C(CH$_3$)$_3$]$_d$ 14. Cellulose—[O(CH$_2$)$_3$NHC(=O)(CH$_2$)$_2$CO(=O)(CH$_2$)$_5$O(CH$_2$)$_5$CH$_3$]$_d$ 15. Agarose—[OCH$_2$C(=O)O(CH$_2$)$_4$—⌬—CH$_2$—⌬]$_d$ TABLE 1-continued Representative Adsorbents d > 2

16. Cellulose—[OC(=O)(CH$_2$)$_{16}$CH$_3$]$_d$

17. Cellulose—[OCH$_2$C(=O)NH(CH$_2$)$_3$NH(CH$_2$)$_3$NHC(=O)SS(CH$_2$)$_7$CH$_3$]$_d$ 18. Cellulose—
   (OC(=NH)NH(CH$_2$)$_{12}$CH$_3$)$_d$
   (O,O-C=N(CH$_2$)$_{12}$CH$_3$)$_d$
   (OC(=O)NH(CH$_2$)$_{12}$CH$_3$)$_d$ 19. Cellulose—[O(CH$_2$)$_2$SO$_2$(CH$_2$)$_2$O(CH$_2$)$_7$CH(CH$_3$)CH$_2$CH(CH$_3$)CH$_3$]$_d$ 20. Polyacrylamide—[C(=O)NHCH((CH$_2$)$_2$—naphthyl)COOH]$_d$ 21. Polyacrylamide—[C(=O)NHCH((CH$_2$)$_{10}$CCl$_3$)COOH]$_d$ 22. Polyacrylamide—[C(=O)NHNHC(=O)(CH$_2$)$_2$C(=O)NH(CH$_2$)$_{18}$CH$_3$]$_d$ 23. Polyacrylamide—[C(=O)NH(CH$_2$)$_2$—C(triazole)—N=N—C$_6$H$_4$—(CH$_2$)$_{10}$CH$_3$]$_d$ 24. Polyacrylamide—[C(=O)NHCH$_2$C(=O)NHCH$_2$C(=O)NHCH(COOH)CH$_2$—C$_6$H$_3$(OH)—N=N—C$_6$H$_4$—(CH$_2$)$_{10}$CH$_3$]$_d$ 25. Polyacrylamide—[C(=O)NH(CH$_2$)$_2$NHC(=O)—C$_6$H$_4$—N=N(CH$_2$)$_{10}$CH$_3$]$_d$ TABLE 1-continued Representative Adsorbents d > 2

26. Polyacrylamide—$\left[ \underset{\|}{\overset{O}{C}}NH(CH_2)_2N\underset{\|}{\overset{O}{H}}C-\underset{}{\overset{}{\bigcirc}}-NH\underset{\|}{\overset{S}{C}}NH(CH_2)_{12}CH_3 \right]_d$ 27. $\underset{NH_2}{\underset{\|}{\overset{C=O}{|}}}\underset{}{\overset{CHCH_2}{|}}\left[ \underset{\underset{CH_3}{\overset{|}{(CH_2)_{12}}}}{\underset{\overset{|}{O}}{\underset{\overset{|}{CH_2}}{\underset{\overset{|}{C}-OH}{CH_2CH}}}}\underset{NH_2}{\underset{\overset{|}{C=O}}{-CH_2CH-}} \right]_d \underset{\underset{CH_3}{\overset{|}{(CH_2)_{12}}}}{\underset{\overset{|}{O}}{\underset{\overset{|}{CH_2}}{\underset{\overset{|}{C}-OH}{-CH_2-CH_2}}}}$ 28. $\underset{OH}{\overset{CHCH_2}{|}}\left[ \underset{\underset{CH_3}{\overset{|}{(CH_2)_{12}}}}{\underset{\overset{|}{O}}{\underset{\overset{|}{CH_2}}{\underset{\overset{|}{C}-OH}{CH_2CH}}}}\underset{OH}{-CH_2CH-} \right]_d \underset{\underset{CH_3}{\overset{|}{(CH_2)_{12}}}}{\underset{\overset{|}{O}}{\underset{\overset{|}{CH_2}}{\underset{\overset{|}{C}-OH}{-CH_2-CH_2}}}}$ 29. Glass—$\left[ O-\underset{Cl}{\overset{Cl}{\underset{|}{Ti}}}-O-(CH_2)_3O(CH_2)_6CH_3 \right]_d$ 30. Glass—$\left[ O\underset{OH}{\overset{OH}{\underset{|}{Si}}}(CH_2)_{12}CH_3 \right]_d$ 31. Glass—$\left[ O\underset{OH}{\overset{OH}{\underset{|}{Si}}}(CH_2)_2NH\underset{\|}{\overset{O}{C}}-\underset{}{\overset{}{\bigcirc}}-NH\underset{\|}{\overset{O}{C}}(CH_2)_{12}CH_3 \right]_d$ 32. Glass—$\left[ O\underset{OH}{\overset{OH}{\underset{|}{Si}}}(CH_2)_2N\underset{\|}{\overset{S}{C}}NH(CH_2)_5-\underset{}{\overset{}{\bigcirc}} \right]_d$ 33. Glass—$\left[ O\underset{OH}{\overset{OH}{\underset{|}{Si}}}(CH_2)_2O(CH_2)_{12}CH_3 \right]_d$ 34. Polystyrene—$\left[ \underset{}{\overset{}{\bigcirc}}-CH_2\underset{\underset{CH_3}{|}}{\overset{\overset{CH_3}{|}}{N^+}}(CH_2)_{12}CH_3 \right]_d$

TABLE 1-continued
Representative Adsorbents
d > 2

35. Styrene-Divinylbenzene
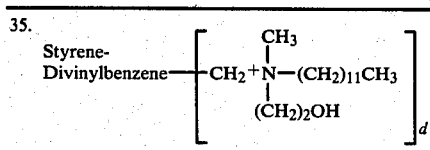

36. Styrene-Divinylbenzene
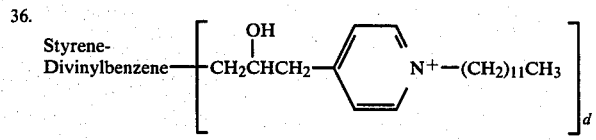

37. Styrene-Divinylbenzene
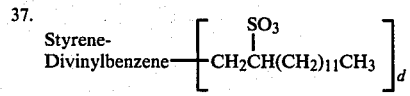

38. Styrene-Divinylbenzene
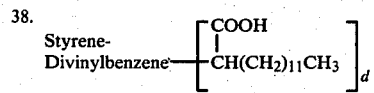

39. Styrene-Divinylbenzene
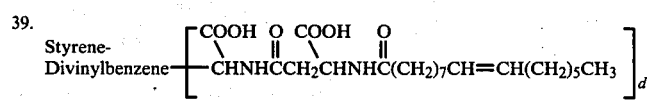

40. Styrene-Divinylbenzene
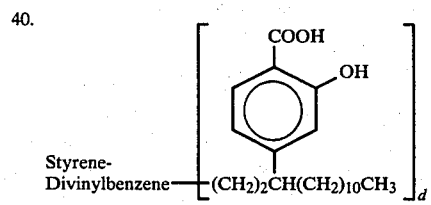

These adsorbents may in general be made by known processes, principally either by copolymerization of hydrophobe-substituted monomers with hydrophilic monomers or by linking the hydrophobes to carriers which are hydrophobic, or which become so by virtue of the linking group residues which contain polar groups. It is preferred to use hydrophilic carriers and to accomplish the hydrophobe linking by use of mild and well-defined linking techniques such as the well-known carbodiimide, cyanogen halide or bisoxirane linking techniques; the reactions are mild and well defined, and the products are stable. A myriad of other suitable synthetic procedures will be readily apparent to the artisen.

The above described adsorbents may be in the physical form of gels; porous films having single or multiple layers; hollow microspheres; solid particles; woven matrices; compressed, randomly aligned fibrous mats; fibrous plugs; or suspensions which may in turn be precipitated by floculating agents, collected on coarse filters or separated by centrifugation. Fibrous mats are preferred.

The adsorbents are typically used by draining the suspension to be purified through an adsorbent membrane, mat or column packed with particles or fibers of the adsorbent. This is preferred over the alternative of simply admixing suspension and adsorbent in bulk and then removing the adsorbent by filtration or centrifugation. Compressed mats, woven matrices or membranes are most suited to situations where the adsorbent will be stressed, while loose, randomly arranged fibrous masses are satisfactory for low pressure embodiments.

A wide range of suspensions may be treated in accordance with this invention. The suspending fluid need not be an aqueous solution but may also be a gas such as air. For example, aerosols of anhydrous lipin particles, oil droplets or aqueous suspensions may be freed of the suspended matter by passage through the adsorbents described herein.

The liquid suspension may also contain lipophilic proteins such as albumin or moderate concentrations of water-miscible organic solvents such as ethanol without significant adverse affect on adsorbent performance. Generally less than 30% v/v of organic solvent in water is acceptable.

The particles to be separated from suspension may be oil droplets, oil-in-water emulsions, viruses, lipin vesicles such as cellular microorganisms, liposomes, animal cells (particularly blood cells) chylomicrons and mixtures of these particles.

The nature and concentration of the particles are not critical but will influence the selection or particular hydrophobe adsorbents and the amounts thereof to be used. The anticipated particle size will bear on the average pore diameter selected for the adsorbent matrix. Generally, the average pore diameter should be about from 1.5 to 10 dwell time and quantity of adsorbent will be unique to each procedure, both parameters are readily determinable by the artisan by simply varying the quantity of adsorbent and the contact time of the suspension to arrive at an optimal separation.

The adsorbents may be used in conjunction with separate filters which act primarily by a sieving mechanism. For example, large, non-lipin particles may first be removed from a crude, bacteria-containing suspension by passage through a conventional depth filter first, followed by the adsorbent described herein, and finally a 0.2 micron pore diameter filter. Thus even though a sterile filter is used one may employ a considerably smaller surface area than heretofore feasible because the bacterial load is reduced or eliminated by the adsorbent, thereby essentially relegating the sterile filter to an insurance role.

Hydrophobe adsorbents may be employed to separate viruses and cellular microorganisms from drinking water, sewage effluent, parental solutions, pharmaceuticals, alcoholic and non-alcoholic beverages. They are useful in diagnostic assays which require the removal of cells or chylomicrons from test samples. They may be employed in synthetic procedures using microorganisms, for example harvesting bacteria or viruses from suspension culture as well as aiding in the cultivation of tissue cultures. Finally, they are effective in removing lipin particles from aerosols. times the average diameter of the particles to be removed from suspension. If a mixture of particles is to be filtered the largest particle should determine the pore diameter. However, layered adsorbents having decreasing pore size may be employed satisfactorily.

It is not essential that the ionic strength or pH of the suspension be modified before contact with the adsorbent, although optimal results are obtained when the adsorbent polar groups, if any, are exposed. Thus, suspensions contacted with cation substituted adsorbents should be at a slightly basic pH, and vice versa for anion substituted adsorbents. However, it may be desirable to thoroughly elute the adsorbent with a prewash of solution having similar ionic content to the suspension to be purified, particularly if ion exchange phenomena are to be avoided during small scale preparative procedures for labile substances such as proteins, or where the ion exchange capacity of the adsorbent could be deleterious to or change the ionic composition of the final product, e.g. as in the case of parenteral salt solutions.

Both the period of time for the suspension to remain in contact with the adsorbent and the comparative amounts of adsorbent and suspension will depend upon the comparative avidity of the adsorbent for the particles of interest in the particular suspending fluid used, the presence and rate of adherence of competitive lipin particles or lipophiles, the particle contamination load and the pore size and hydrophilicity of the adsorbent matrix. Thus while the All cellular microorganisms are capable of adsorption to a lesser or greater degree by the hydrophobe adsorbents described herein. Examples include mycoplasma and organisms of the families Pseudomonadaceae, Micrococcaceae, Lactobacillacea, Corynebacteraceae, Achromobacteraceae, Enterobacteraceae, Parvobacteraceae, Spirochaetaceae and Treponemataceae. Animal viruses such as cytomegalovirus, herpes virus group, influenza and rubella are also bound, as are yeasts.

The purpose of the adsorbents in sewage treatment is primarily to reduce rather than eliminate the potentially infectious bioburden. Hence, flat surfaced adsorbents or matrices having large pore sizes in the range of 100–750 microns are preferable because of the large bulk of suspended particles typically encountered; a proportion of these particles, for example cellulose fibers, inorganic particles and the like, are relatively innocuous and need not be retained. The carrier and linking groups should not be susceptible to hydrolysis or other deleterious changes brought on by enzymes found in sewage; polyolefin carriers are preferred over polysaccharides for this reason.

Hydrophobe adsorbents are effective in removing viruses and bacteria from drinking water. Hence it is preferred to use adsorbents which carry strong ion exchange functions, particularly positively charged groups such as quaternary ammonium, and that the ion exchange function be situated adjacent to the hydrophobe. Ideally, the hydrophobe is covalently bonded either directly into the ion exchange group or to an atom to which the ion exchange group also is bound. The carrier need not be hydrophilic but it is desirably substituted with weakly polar groups as described above. Hydroxy-substituted polymers are preferred. Since the identity of the viral and bacterial contaminants is usually unknown it is preferred to employ a mixture of discrete adsorbents, some of which carry exposed positive charges and others of which have exposed negative charges. Also suitable are amphoteric adsorbents, where the both positive and negative charges are present in the same hydrophilic macromolecule. Where the adsorbent is employed in divided form rather than a formed article it is generally unnecessary to aid the separation of suspended adsorbent from suspension by use of floculating agents.

Hydrophobe adsorbents may also be used to entrap microorganisms in therapeutic solutions to be administered to animals, whether during manufacturing of the solutions or in their administration. These solutions are predominantly parenteral and peritoneal dialysis solutions containing salts, carbohydrates or proteins, for example saline, amino acids solutions, KCl solutions, 5% dextrose, and blood protein fractions such as antihemophilic factor, prothrombin complex, albumin, activated prothrombin complex, insulin, hemoglobin and plasma protein fraction. Antihemophilic factor (AHF) concentrates typically contain AHF at greater than 3 times the activity in normal plasma per unit weight of protein. Hydrophobe adsorbents are especially useful where the therapeutic solution is labile to conventional sterilizing agents such as heat and ethylene oxide, or contains a hydrocolloid. Examples of the former include some antibiotics, amino acid and carbohydrate mixtures, proteins and polypeptides, while the latter include proteins, dextrins and cellulose ethers.

The selection of hydrophobe adsorbent and its physical conformation will primarily depend upon the therapeutic solution to be filtered. It is generally preferred to use adsorbents having substantially nonionogenic character—particularly with protein-containing parenterals. However, strongly ionic adsorbents containing physiologically acceptable ions are suitable for use with most therapeutic solutions where the adsorbent has been prewashed with a representative sterile aliquot of the solution, thereby neutralizing the ion exchange activity with respect to that particular solution. However, there may be certain instances where the ion exchange will be beneficial, for example demineralization of carbohydrate solutions using amphoteric exchangers. Here ion exchange and hydrophobe adsorption activity can be advantageously combined into one processing step. Finally the exposed polar groups of the adsorbent should carry the same charge as the net charge of the therapeutic solute.

The intended mode of administration of the therapeutic solution—peritoneal, intravenous infusion, injection or oral—generally is not material to the selection of adsorbent at the manufacturing level. Table 1 adsorbents 1, 3, 8 and 16 are preferred, with the adsorbents 1 and 3 most preferred. They are most advantageously employed as membranes, woven fabrics or random, fibrous masses having an average pore diameter of about from 0.75 to 20 microns, preferably about from 1.5 to 10 microns.

The same adsorbents may be used when administering the solutions to patients. This is conveniently accomplished by including the adsorbents in administration sets. These sets usually include (a) a conduit terminating at one end with a means for connecting the conduit to a container of the solution and at the other end with a means for entering the body of the animal and (b) a filter interposed in said conduit between said both means.

The means for entering the body include needles, and venous or peritoneal catheters. Flow control devices and connectors for the multiple attachment of parenteral solution containers are frequently included in such sets. Hydrophobe adsorbents can be used in place of the filter or interposed between the filter and the solution container as an adjunct to the filter. The hydrophobe adsorbent is preferably the sole filter when protein-containing parenteral solutions such as antihemophilic factor are to be administered, because the average pore size may be increased to about from 2 to 20 microns from the usual 0.2 to 0.5 microns, thereby increasing the filter flux. Further, air block formation is reduced by the hydrophobe adsorbents when compared to the wholly hydrophilic filters previously employed. Thus the complex dual filters which have been proposed to ameliorate this problem may be replaced by unitary, hydrophobe absorbent filters.

The capacity of the hydrophobe adsorbents for hepatitis is generally superfluous when treating blood protein-containing pharmaceuticals. The starting plasma has been screened for assayable hepatitis and, in the case of products such as albumin, heat treated to destroy the virus. Other parenteral solutions are free of hepatitis virus because no potentially infective substance is used as a starting material. However, while such products are essentially free of assayable hepatitis it is desirable to remove other viruses that may be present and are not screened for, e.g. herpes and rhinoviruses.

The hydrophobe adsorbents are also useful in the pasteurization of alcoholic beverages, primarily beer and wine. Such products are difficult to pasteurize in a manner which does not also deleteriously affect the beverage quality. Surprisingly, it has been found that ethanol concentrations in aqueous solutions of up to about from 0.5% to 30% do not significantly interfere with the capacity of the hydrophobe adsorbents to bind yeast and bacteria suspended in such solutions.

In accordance with this invention, beer and wine ordinarily are pasteurized by simply passing the fermentate through a matrix of hydrophobe adsorbent. The average pore diameter here will be larger than with filters having the primary task of removing bacteria because the yeast cells are comparatively larger. A suitable pore diameter ranges about from 3 to 20 microns. Ion exchange adsorbents may be used, keeping in mind the caveats expressed above regarding parenteral solutions. The same embodiments as were discussed above in connection with hydrocolloid solutions are satisfactory in pasteurizing alcoholic beverages.

The preceding discussion has focused on microbes as contaminants, where their removal ordinarily is followed by their destruction. The hydrophobe adsorbents, however, also are extremely useful in recovering cells from suspension culture or mammalian cell culture. The adsorbents are most useful in the first embodiment. Here a microbe, generally a bacterium, is cultured in suspension in a nutrient solution, ordinarily through the end of the log growth phase. Then a substrate solution is applied to a column of hydrophobe adsorbed organisms and product drawn off as column eluate. Preferably the solution contains no general growth factors such as carbohydrates or nitrogen sources. Products which may be manufactured by this technique or by fluidized bed fermentations include fructose, various amino acids, nucleotides, penicillin, and staphylococcal protein A.

Surface adhering cells such as mammalian cell lines from disaggregated organs also may be cultured simply by agitating finely divided adsorbent in a nutrient medium inoculated with the cells. The cells are separated from suspension by centrifuging or filtering the adsorbed cells. They may then be used in the same way as bacteria supra or in applications unique to animal cells, e.g., artificial organs or in the synthesis of unique products such as antibodies by hybridoma cells and viruses for vaccine production.

The adsorbed lipin particles, whether cells, liposomes or viruses, also can be desorbed for their recovery or for regeneration of the adsorbent. This may be accomplished by (a) cleaving the linking group as described above, (b) introducing solvents having nonpolar groups in place of or as a substantial proportion of the eluting solvent, or (c) adding other lipin particles to displace the adsorbed materials. For example, virions may be recovered for vaccine preparation or other uses by eluting the adsorbent with an aqueous solution of salt and a high concentration, i.e., a greater than 30% v/v, of a lipophilic solvent such as ethylene glycol, acetone, ether or alkanol. Recovery of the adsorbent is facilitated if the solvent is also water soluble. Forty percent ethylene glycol in saline is preferred. Alternatively, a saline suspension of liposomes prepared in known fashion may be passed through the matrix and the virions recovered from the aqueous phase after removing the eluted liposomes, e.g. by centrifugation or extraction of the liposomes into an immiscible solvent.

Finally, hydrophobe adsorbents greatly facilitate diagnostic assays for analytes in lipemic samples of plasma or serum. The opaque, milky appearance of such samples and the difficulty with their use is optical assays is largely a function of chylomicrons. The chylomicrons can be adsorbed simply by passing the sample through a matrix of hydrophobe adsorbent, preferably in conjunction with a serium skimmer. Serum skimmers are disclosed in U.S. Pat. Nos. 3,799,342 or 3,865,731. Their salient features are a filter for removing the insoluble constituents of serum and a chamber for collecting filtered serum or plasma. They are used to skim serum from collection tubes in which collected blood samples have been allowed to clot. These devices generally comprise a collection receptacle for filtered sample, a valve which permits the sample to flow into the collection receptacle but not in the opposite direction, a filter disposed on the opposite side of the valve from the receptacle and a flexible sealing member for engaging the inner surfaces of the test sample container. The device is used by pushing it into the test sample container, usually a collection tube containing clotted blood. The sealing member prevents passage of fluid between the skimmer and the walls of the collection tube. Instead, the sample flows through the filter and one-way valve into the receptacle. The improvement of this invention comprises using a hydrophobe adsorbent in such devices as the filter, or as an element thereof. Preferably the entire filter is nonwoven plug or mat of fibrous hydrophobe adsorbent having an average pore diameter from about 15 to 100 microns. A large pore diameter of about 75 microns is considered optimal because the rapid passage of plasma or serum facilitated by such an open network reduces the adsorption of high density and low density lipoproteins. Smaller pore diameters are acceptable if lipoprotein assays are not contemplated. The sample may then be assayed for an analyte using a procedure in which chylomicrons ordinarily would interfere, for example in optical assays as defined above.

The hydrophobe adsorbents are particularly useful for screening aerosol-borne lipin particles from air. The maintenance of sanitary, or particle-free atmospheres in hospital operating rooms, sterile product manufacturing and electronics assembly operations is paramount. Hydrophobe adsorbents are effective in screening oil droplets and microorganisms from the air supplies used in such environments, whether or not the aerosols contain water. The adsorbents may be employed with conventional passive filters to collect any nonlipin materials. The adsorbents may be regenerated by washing thoroughly with a volatile organic solvent or by hydrolysis or reduction of linking groups as described above.

The invention will be more fully understood upon reference to the following Examples.

EXAMPLE 1

Preparation of adsorbent 1, Table 1. 5 g of nylon wool (sold by the Fenwal Division of Travenol Laboratories for the affinity collection of granulocytes) was immersed in a 400 ml of an emulsion containing 350 ml distilled water and 50 ml of 1,4-butanediol diglycidyl ether and stirred for 2.45 hours. After decanting, but without rinsing, 100 ml octylamine were added and stirred for one hour. Both reactions were conducted at 22° C. A white, oily precipitate was eluted from the substituted nylon under extensive washing with distilled water. The product was soft and felt oily to the touch. A 20 ml syringe was packed to the 5 ml mark with adsorbent and rinsed exhaustively. The effect of an ethanol rinse was evaluated by rinsing a packed syringe with 30 ml ethanol followed by 30 ml of distilled water. The ability of the adsorbent to removed bacteria was assayed by adding 25–30 ml of contaminated normal serum albumin to the syringe and allowing the albumin to passively flow through the filter. This albumin was heavily infected with flora indigenous to the blood plasma fractionation facility from which it was obtained, primarily thought to be Pseudomonas sp. in populations greater than $10^6$ organisms/ml. The last 5 ml were collected, diluted as indicated and aliquot plated onto culture media. The results are shown in Table 2 below.

TABLE 2

| | Adsorbent | Eluted Bacteria/ml |
|---|---|---|
| water washed | none | TNTC* at 1:100 dilution |
| | unsubstituted nylon | TNTC at 1:100 dilution |
| | modified nylon | 0 |
| ethanol washed | unsubstituted nylon | TNTC at 1:100 dilution |
| | modified nylon | 32 |

*Too numerous to count.

EXAMPLE 2

Preparation of adsorbent 3, Table 1. 5 g of nylon wool from the same source as Example 1 was immersed into 400 ml of an emulsion containing 350 ml distilled water, 5.5 g N,N[1]-dicyclohexylcarbodiimide and 50 ml of octanoic acid, then reacted for 1 hour at ambient temperature while stirred. The firm, modified nylon was washed with distilled water, but unlike Example 1 no precipitate eluted. An ethanol washed column was also prepared as in Example 1, and the bacterial retention qualities evaluated in the same fashion with contaminated normal serum albumin. Bacterial adsorption was satisfactory.

EXAMPLE 3

The performance of the Example 1 modified nylon was evaluated using additional suspending fluids and fully characterized contaminant organisms. The organisms designated in Table 3 below were seeded at the indicated populations into sterile phosphate buffered saline (PBS), 5% normal serum albumin (NSA), distilled water, pasteurized whole milk and beer (Coors). Plugs of modified and unmodified (control) nylon were placed into a 12 ml syringe and washed with 15 ml of sterile heart infusion broth. Three ml of each contaminated liquid were then passed through the syringes and the eluate bacterial population determined by promptly plating the eluate onto culture media in conventional fashion. The results are reported in Table 3.

TABLE 3

| | | Bacteria/ml | | |
|---|---|---|---|---|
| Medium | Organism | Inoculum | Control Eluate | Test Eluate |
| PBS | *S. aureus* | 320,000 | 72,000 | 1 |
| | *P. diminuta* | 120,000 | 24,000 | 0 |
| Water | *S. aureus* | 330,000 | 39,000 | 3 |
| | *P. diminuta* | 50,000 | 41,000 | 0 |
| Milk | *S. aureus* | 480,000 | 67,000 | 24,000 |
| | *P. diminuta* | 140,000 | 33,000 | 32,000 |
| Beer | *S. aureus* | 440,000 | 8,000 | 140 |
| | *P. diminuta* | 80,000 | 29,000 | 0 |
| NSA | *S. aureus* | 280,000 | 69,000 | 2 |
| | *P. diminuta* | 80,000 | 39,000 | 0 |
| | *B. subtilis* | 30,000 | 11,000 | 90 |

It was concluded from Table 3 that hydrophobe adsorbents are capable of multifold reduction or elimination of the microbial burden of a wide variety of contaminated liquids. This effect is accentuated by electrostatic or mechanical seiving by the nylon matrix as evidenced by the lowered populations in the control eluates. The small reduction in milk contamination is believed to be the result of competitive binding of the hydrophobes by lipid vesicles and residual flora endogenous to the milk after pasteurization; an increased amount of adsorbent would remove both of these components as well as added bacteria. Parallel experiments with a yeast, *Saccharomyces cerevisiae* also were conducted. The modified nylon was somewhat more effective than the control in removing the contaminants from PBS, NSA, water and beer, but with milk the control was effective as the modified nylon. This was attributed to the likelihood that the yeast was considerably larger than bacteria and predominately filamentous, therefore mechanically retained by the nylon control.

EXAMPLE 4

Satisfactory removal of *E. coli* from saline suspension could be achieved upon repeating Example 3 with granules of adsorbent 34 described in Table 1 above.

EXAMPLE 5

Satisfactory removal of *Streptococcus faecalis* (predominantly diploid) in serum broth could be achieved upon repeating Example 1 with 10–50 U.S. mesh beads of adsorbents 20,21,25,29 or 30 described in Table 1 above.

EXAMPLE 6

Mycoplasma prepared in known fashion and suspended in isotonic nutrient broth could be satisfactory adsorbed upon passage through adsorbent 16, Table 1, in the form of five layers of cotton cloth.

EXAMPLE 7

Adsorbent 4 prepared from hardwood sawdust and sandwiched at a thickness of 200 mm between two fine-mesh stainless steel screens could remove endogenous microorganisms, primarily coliforms, from raw sewage.

EXAMPLE 8

*Acanthamoeba castellani*, a soil amoeba, could be removed from a growth medium containing 1.5% glucose and 1.5% proteose peptone by passage of the suspension through a cotton fiber plug of adsorbent 9, Table 1.

EXAMPLE 9

An aerosol of a saline suspension of *E. coli* produced by a household vaporizer could be screened from a 1:100 dilution in humidified air by blowing the aerosol at a rate of 1 cubic foot/min through a $5\times15$ cm column packed loosely with a adsorbent 3, Table 1, in the form of modified nylon fibers.

EXAMPLE 10

5 ml of lipemic human serum could be clarified by the conventional use of an Accu-sep serum skimmer in which the filter was replaced by adsorbent 4, Table 1, in the form of a matted cellulose fiber plug.

EXAMPLE 11

Phospholipid vesicles were prepared according to the procedure of Batzri et al., "Biochem. Biophys. Acta" 298:1015–1019 (1973) using diacetyl phosphate to render the bilayer vesicles negatively charged. The vesicles could be adsorbed by briefly mixing adsorbent 11 of Table 1 with the suspension and centrifuging.

EXAMPLE 12

This example is concerned with the continuous manufacture of streptokinase from immobilized streptococci. A 5 liter column was packed with polyacrylamide beads modified as adsorbent 21, Table 1. Hemolytic streptococci were cultured as described in U.S. Pat. No. 3,855,065 and a 1 liter inoculumn of log phase organisms introduced onto the column, followed by a steady flow of 75 ml/hour of a nutrient medium containing 8% corn steep liquor and 7% Cerelose in water. The column eluate was collected for 24 hours and the streptokinase recovered by precipitation with ammonium sulfate. The columns would function satisfactorily until microbial replication clogged the pores and restricted flow or until the column adsorptive capacity became overloaded and effluent break out occurred. The column lifetime may be extended by substituting saline for nutrient medium after 3 hours' cultivation.

EXAMPLE 13

Example 2 of U.S. Pat. No. 3,821,086 is followed by the manufacture of fructose from glucose except that the Primafloc C-7 employed by the patentee to insolubilize the Arthrobacter species was substituted by adsorbent 17, Table 1, as modified course hardwood sawdust. When enzyme activity declined to an unacceptable level the adsorbent could be recycled by reducing the adsorbent with an aqueous solution of 0.5 M dithiothreitol and 0.001 M EDTA for 2 hours, washing the adsorbent extensively with distilled water, and reacting the adsorbent with dioctyldisulfide under oxidizing conditions regenerate the adsorbent.

EXAMPLE 14

Adsorbent 3, Table 1, as a modified nylon wool was loosely packed into a polyethylene flattened cylinder containing 3 cc volume. This filter assembly could be satisfactorily used in the continuous ambulatory peritoneal dialysis equipment disclosed in copending U.S. patent application Ser. No. 27,419 as an adjunct to or in place of the particulate filter 26 described in that application.

EXAMPLE 15

Herpes virus type 1, strain hf was recovered from MA104 cell culture and the suspension adsorbed upon passage of 5 ml of suspension through a 1 ml volume plug of either of the adsorbents employed in Example 1 or 2. Adsorption was evaluated by serially diluting the adsorbent eluate, inoculating monolayer MA104 cell cultures with the dilutions and observing for cytopathic effects.

EXAMPLE 16

1.5 g of nylon fibers were packed into a 1-inch diameter filter holder, mixed overnight with about 15 ml of concentrated acetone solution of bis-epoxide. Then an aqueous solution of linear dextran (average 200,000 D) at saturation is mixed with the activated fibers for 24 hours at pH 9. The product is rinsed with copious quantities of cold distilled water and brought to dryness with 50%, 70%, and then 95% acetylnitrile followed by acetone. Then 100 mg cyanogen bromide in ice cold water (pH 9) is mixed slowly with the modified nylon and the pH maintained with NaOH. When no more NaOH was required, a saturated solution of n-octyl amine is mixed overnight with the activated matrix. The following day, the system is washed extensively with water and then 0.5 M ethanolamine. A suspension of $1\times10^5$ *Pseudomonas diminuta* organisms in demineralized water was allowed to percolate through the filter. The bacteria were satisfactorily adsorbed.

I claim the following:

1. A method for removing lipin particles from suspension in a fluid, comprising contacting the suspension with an adsorbent composition having the formula $[(Y)_eB]_dZ$ wherein Y is a hydrophobic ligand, B is a strong ionogenic group, Z is a water insoluble carrier, e is an integer and d is greater than 2 under conditions to adsorb the particles, followed by separating the compositions from the fluid.

2. The composition of claim 1 wherein Y is a group having the formula

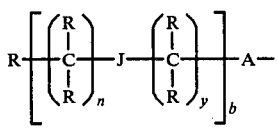

and wherein
- R is hydrogen, nitro, alkyl, alkyl ether, halogen, monocyclic aromatic hydrocarbon or a carbocycle system;
- A is a bond, monocyclic aromatic hydrocarbon or carbocycle system;
- b is an integer;
- J is oxygen, sulfur or a bond; and
- n and y are zero or an integer;

with the proviso that where A is a bond and R is hydrogen, nitro or halogen then the sum of n and y is an integer greater than 5.

3. The composition of claim 2 wherein R is alkyl having about from 1 to 6 carbon atoms.

4. The composition of claim 2 wherein the sum of n and y is 8, R is hydrogen, J and A are bonds and e and b are both 1.

5. The composition of claim 1 wherein Y is normal alkyl having from 6 to about 20 carbon atoms.

6. The conposition of claim 1 wherein Y is phenyl.

7. The composition of claim 1 wherein B and Z together are hydrophilic.

8. The composition of claim 1 wherein Z is an organic polymer.

9. The composition of claim 8 wherein the polymer contains strong ionogenic groups which are not substituted with a hydrophobic ligand.

10. The composition of claim 9 wherein the group is sulfonyl or quaternary amino.

11. The composition of claim 1 wherein Z is inorganic.

12. The composition of claim 11 wherein Z is glass.

13. The composition of claim 1 wherein e is 1.

14. The method of claim 1 wherein the fluid is an aqueous ligand.

15. The method of claim 14 wherein the liquid has an ionic strength of less than about 0.1.

16. The method of claim 15 wherein the liquid contains about from 1 to 30% protein (w/v).

17. The method of claim 14 wherein the particles are viruses.

18. The method of claim 1 wherein the adsorbent is a formed article.

19. The method of claim 1 wherein the adsorbent is woven or a membrane.

20. The method of claim 1 wherein the adsorbent is a fibrous mass.

21. The method of claim 1 wherein Z is an organic polymer and d ranges about from 0.5 to 0.1 times the number of monomer units constituting the polymer.

* * * * *

UNITED STATES PATENT AND TRADEMARK OFFICE
CERTIFICATE OF CORRECTION

PATENT NO. : 4,411,795

DATED : October 25, 1983

INVENTOR(S) : Wayne P. Olson

It is certified that error appears in the above-identified patent and that said Letters Patent are hereby corrected as shown below:

Column 1, line 38 change "A" to -- $\overset{o}{A}$ --.

Column 4, line 43, change the R-N+(CH$_3$)$_3$X to -- R-N$^+$(CH$_3$)$_3$X --.

Column 6, line 1, please change "40 A" to -- 40 $\overset{o}{A}$ --.

Column 6, line 2, please change "15 A" and "10 A" to -- 15 $\overset{o}{A}$ -- and --10 $\overset{o}{A}$ -- respectively.

Column 17, line 43 change "hydrophobic" to --hydrophilic--.

UNITED STATES PATENT AND TRADEMARK OFFICE
CERTIFICATE OF CORRECTION

PATENT NO. : 4,411,795

DATED : October 25, 1983

INVENTOR(S) : Wayne P. Olson

It is certified that error appears in the above-identified patent and that said Letters Patent is hereby corrected as shown below:

Column 18, line 64, move from "dwell time.......aerosols." through (column 19, line 25) and insert the same after "Thus while the" in column 19, line 54.

Column 22, line 27, please underline supra

Column 22, line 58, "serium" to read -- serum --.

Column 23, line 58, "removed" to read -- remove --.

Column 26, line 17, "course" to read -- coarse --.

Column 6, line 5, "15 A" should read -- 15 $\overset{o}{A}$ --.

Signed and Sealed this

Third Day of July 1984

[SEAL]

Attest:

GERALD J. MOSSINGHOFF

Attesting Officer     Commissioner of Patents and Trademarks